United States Patent [19]

Sugimoto

[11] Patent Number: 4,568,880
[45] Date of Patent: Feb. 4, 1986

[54] DIAGNOSTIC APPARATUS FOR UTILIZING NUCLEAR MAGNETIC RESONANCE

[75] Inventor: Hiroshi Sugimoto, Tochigi, Japan

[73] Assignee: Tokyo Shibaura Denki Kabushiki Kaisha, Kawasaki, Japan

[21] Appl. No.: 526,277

[22] Filed: Aug. 25, 1983

[30] Foreign Application Priority Data

Aug. 31, 1982 [JP] Japan ................................ 57-150975

[51] Int. Cl.$^4$ ............................................ G01R 33/20
[52] U.S. Cl. ................................... 324/309; 324/307; 324/318
[58] Field of Search ............... 324/300, 307, 311, 309, 324/318, 319, 320

[56] References Cited

U.S. PATENT DOCUMENTS 3,932,805  1/1976  Abe ................................... 324/309
4,318,043  3/1982  Crooks ............................. 324/309

Primary Examiner—Michael J. Tokar
Attorney, Agent, or Firm—Cushman, Darby & Cushman

[57] ABSTRACT

In a apparatus for examining an object by nuclear magnetic resonance to produce images of cross-sectional slices of the object, it necessarily requires to have "a wait time" so as to repeat the applications of the RF pulses toward a plurality of such slices during one examination cycle. A plurality of coil pairs is arranged along the longitudinal axis of the object, and each pair is selectively energized so as to apply to the plurality of slices one of a plurality of gradient fields in conjunction with the steady magnetic field. A plurality of nuclear magnetic resonance signals may be obtained from a plurality of slices during one examination cycle.

7 Claims, 13 Drawing Figures

F I G. 7
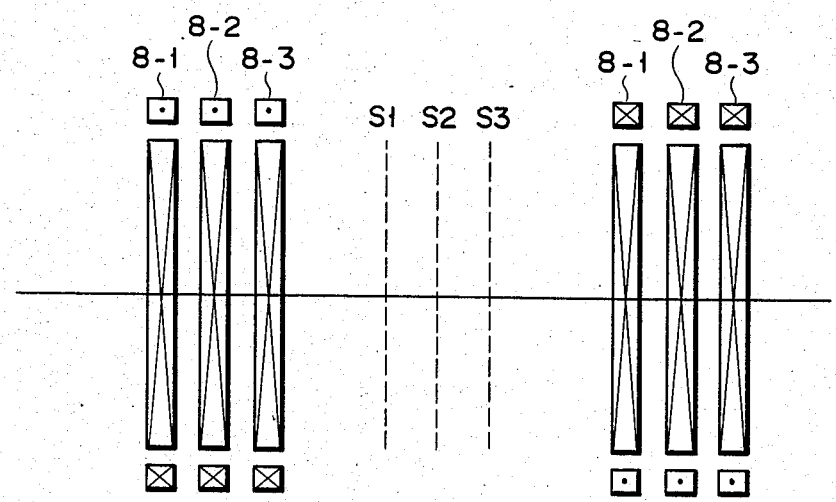
F I G. 8
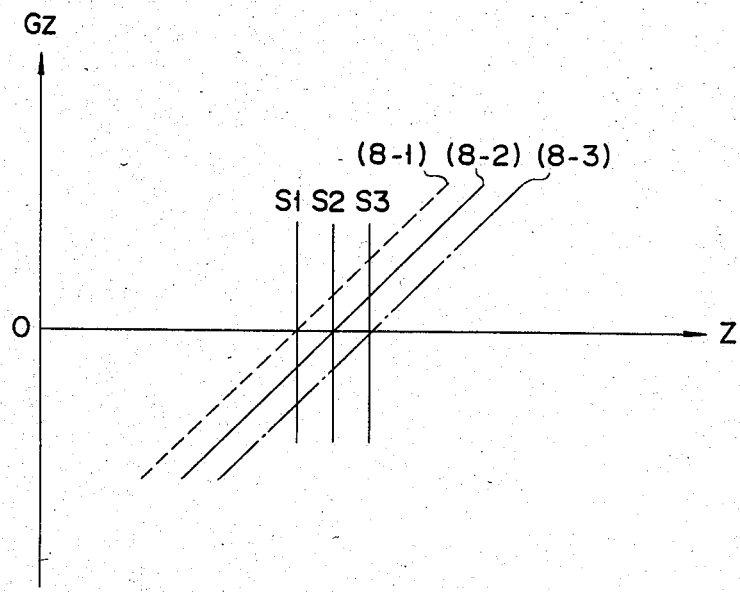

DIAGNOSTIC APPARATUS FOR UTILIZING NUCLEAR MAGNETIC RESONANCE

BACKGROUND OF THE INVENTION

I. Field of the Invention

The present invention relates to a diagnostic apparatus wherein a density distribution of a specified proton (generally, hydrogen nucleus) in biological tissue is measured externally from the object examined (i.e., a patient) in a non-invasive manner by utilizing a nuclear magnetic resonance phenomenon so as to obtain information for medical diagnosis.

II. Description of the Prior Art

Such a diagnostic apparatus is described in e.g., U.S. Pat. No. 4,254,778.

The known nuclear magnetic resonance techniques (referred to "NMR" techniques) will now be described with reference to FIGS. 1 through 5.

A steady magnetic field is generated by an air coil C1 shown in FIGS. 1A and 1B, and a magnetic gradient field is generated by gradient field generating coils C2, C3 and C4 (FIGS. 2 and 3) assembled together with the air coil C1. FIG. 4 shows the fields illustrated diagrammatically in the side elevation in relation to a patient P. A steady field $H_0$ generated by the air coil C1 is superimposed in advance on a gradient field $G_z$ by the coils C2. The gradient field $G_z$ can be obtained by flowing reverse currents through a pair of Helmholtz coils C2 shown in FIG. 2. This coil pair is called "a Maxwell pair". The gradient field $G_z$ has the same direction (z-axis) as that of the steady field $H_0$ and has a zero magnetic intensity on a central plane (perpendicular to the z-axis) between the pair of coils C2 so that the absolute values of the intensities of reverse field components linearly increase in opposite directions from the above-described central plane along the z-axis (FIG. 4). The patient P is then placed in the resultant magnetic field. A selective exciting pulse $H_1$ having a proper frequency component is applied to the patient P through a pair of saddle-shaped probe head coils C5. The selective exciting pulse $H_1$ has a center frequency of 4 MHz (corresponding to a magnetic field of 1,000 gausses for a hydrogen nucleus) of a carrier wave and is obtained by amplitude-modulating an RF pulse by a SINC function. When the selective exciting pulse $H_1$ is applied to the patient P, resonance occurs in a plane region (cross-sectional slice region with respect to the Z axis) wherein a frequency corresponding to a vector sum of the steady field $H_0$ and the gradient field $G_z$ becomes equal to the frequency of the selective exciting pulse $H_1$. A gradient field $G_R$ obtained by a sum of vector components of gradient fields $G_x$ and $G_y$ ($G_x$ and $G_y$ are perpendicular to each other and to $G_z$) respectively generated by the gradient field generating coils C3 and C4 is applied to the slice region (i.e., chosen slice region) where resonance occurs. In this condition, when a free induction decay signal FID is measured through the probe head coil C5, this signal corresponds to a signal obtained by Fourier-transforming a projection signal indicating a specific nucleus density distribution in the direction of the gradient field $G_R$ within the slice of the patient P. The direction of the gradient field $G_R$ can be varied within the x,y plane by changing the relative ratio of intensity of the field $G_x$ generated by the coils C3 to that of the field $G_y$ generated by the coils C4. A resultant free induction decay signal FID is subjected to inverse Fourier transformation, thereby obtaining projection signals in various directions in the x,y plane. By utilizing these projection signals, an image indicating the density distribution of the specific nucleus within the slice of the patient P is obtained.

The following problems are presented in a conventional diagnostic apparatus of this type utilizing nuclear magnetic resonance.

It is generally known that the free induction decay signal FID attenuates as a function of a spin-spin relaxation time "$T_2$". The signal FID from the hydrogen nucleus of the patient attenuates within about 20 to 50 msec. On the other hand, until the protons become aligned again with the steady field $H_0$ to restore the condition that existed before the selective excitation pulse $H_1$ was applied, a so-called "wait time" corresponding to three to five times the spin-lattice relaxation time "$T_1$" is required, the relaxation time "$T_1$" being generally longer than the relaxation time "$T_2$". For this reason, when the selective exciting pulses $H_1$ are successively applied to the patient P without providing sufficient time intervals therebetween, a saturation phenomenon occurs, so that the amplitude of the free induction decay signal FID becomes low, resulting in a low S/N ratio. In other words, although the value of the spin-lattice relaxation time $T_1$ varies in accordance with the examined portions and the individuals examined, the spin-lattice relaxation time $T_1$ takes at least 200 msec. Thus, for example, if the "wait time" is preset to be three times the spin-lattice relaxation time $T_1$, a wait time of at least 600 msec is required for each slice, resulting in the prolongment of each examination time. In order to shorten the wait time, an RF pulse is applied to forcibly orient the protons toward the steady field in the above-described U.S. Pat. No. 4,254,778. However, the wait time cannot be completely eliminated.

From the medical point of view, diagnosis can almost impossible with a single CT image. In a general diagnosis, a plurality of CT images adjacent to a diseased portion are also required. However, as described before, the wait time is necessarily required between two projection operations. Therefore, the time required to complete a single examination time is longer than that in the X-ray CT (computerized tomography), so that much time is wasted in order to obtain several tomographic images.

It is an object of the present invention to provide a diagnostic apparatus utilizing nuclear magnetic resonance wherein the wait time is substantially eliminated during projection signal measurement, and a plurality of tomographic images from the object to be examined can be obtained almost simultaneously.

SUMMARY OF THE INVENTION

The objects stated above may be accomplished by providing a diagnostic apparatus utilizing nuclear magnetic resonance techniques, comprising means for applying to the object a steady magnetic field along a longitudinal axis thereof, first coil means including a plurality of coil pairs, each of which is arranged along said longitudinal axis and is selectively energized so as to apply selectively to the object one of a plurality of first gradient fields, which in conjunction with said steady field gives a predetermined field in one of a plurality of slices of said object, the field direction of which first gradient fields being parallel to that of said steady magnetic field and the field strength thereof changing linearly in an opposite manner along said longitudinal axis, means for oscillating RF pulses and applying the same through probe head means to at least one of said slices of the object in a direction perpendicular to said longitudinal axis so as to excite a nucleus in one of said slices to which is being applied said predetermined field combined between the steady magnetic field and the first gradient field, the probe head means detecting a nuclear magnetic resonance signal derived from one of said slices of the object, second coil means for applying selectively one of a plurality of second gradient fields to one of said slices after application to each of said first gradient field to the same is completed, the field direction of the second gradient field being parallel to said steady magnetic field and the strength of the second gradient field being gradient at a right angle with respect to that of said steady magnetic field, and reconstruction means which receives the nuclear magnetic resonance signals obtained from one of said slices through said probe head means with respect to a plurality of projection directions corresponding to the direction of said plurality of second gradient fields, and reconstructs a plurality of computerized tomography images for the nuclear density of said plurality of slices based upon the nuclear magnetic resonance signals.

The present invention has the effect of providing a diagnostic apparatus utilizing nuclear magnetic resonance wherein the wait time is substantially eliminated during projection signal measurement, and a plurality of tomographic images of an object to be examined can be obtained almost simultaneously.

BRIEF DESCRIPTION OF THE DRAWINGS

The invention can be best understood with reference to the accompanying drawings in which:

FIG. 7 shows an illustrative representation of the $G_z$ coils according to the invention;

FIG. 8 is a graphic representation of the gradient field strength of the $G_z$ coils in FIG. 7;

DETAILED DESCRIPTION OF THE PREFERRED EMBODIMENTS

Figure 1A:
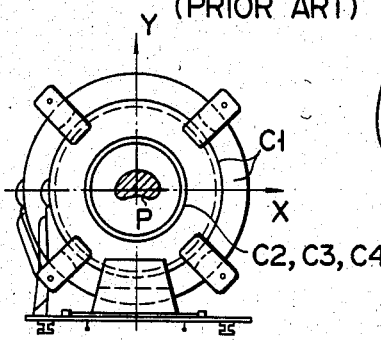
FIG. 1A shows a front view of an air coil employed in the conventional NMR apparatus.

Before proceeding with the various types of the preferred embodiments, the fundamental operations of the diagnostic apparatus utilizing NMR techniques in accordance with the present invention will now be explained.

A diagnostic apparatus according to one principle of the present invention comprises the above-described conventional arrangements i.e., $H_0$ field, $H_1$ pulse and $G_z$ fields, and has special features that the other gradient field $G_R$ (composed by $G_x$ and $G_y$ fields) can be shifted along the Z axis so that the projection directions (angles) for the slice region where the resonance occurs can be chosen by adjusting the relative field strength between the $G_x$ and $G_y$ fields. These $G_x$ and $G_y$ fields are generated by a plurality of coil pairs aligned along the Z axis.

By way of example, assume that four slice regions of the object are to be examined, four different angles (directions) are chosen, i.e., 0°, 90°, 180° and 270° with respect to x,y plane, and one complete examination cycle consists of four examination periods.

During the first examination period, four nuclear magnetic resonance signals can be successively received from the first, second, third and fourth slice regions by applying $G_R$ fields to those regions in turn, while those regions are successively excited by the $H_1$ pulse and $G_z$ fields. The projection angle when applying the $G_R$ fields is kept constant e.g., at 0° during this period. It should be noted that a selection of these slice regions can be effected by switching the energizing currents flowing through the coil pairs. Then a similar operation is carried out during the second examination period, and the projection angle of the $G_R$ field is also kept constant, but at a different angle, e.g., at 90°. Subsequently the third and fourth examinations are successively carried out at different angles e.g., 180° and 270° respectively. After the fourth examination period, one complete examination cycle is accomplished. Consequently four different slice regions can be examined substantially simultaneously within one examination cycle.

A diagnostic apparatus according to a second principle of the present invention has the following features and is operated under the same arrangements as those in the first principle. That is, during one examination period the projection angles of the $G_R$ field application are different from each other. For example, during the first examination period, the $G_R$ field is applied to the first slice region at 0° so as to receive the first nuclear magnetic resonance signal, then the second slice region is applied by $G_R$ field at 90°, thereafter the third slice region is at 180° and finally the fourth slice region is at 270°. During the next scanning period, the $G_R$ field is applied to the first slice region at different angles from that in the first period, e.g., 90°, the second angle is at 180°, the third one is at 270° and the final one is at 0°. After completing four examining periods one complete examination cycle can be realized.

It should be noted that the nuclear magnetic resonance signal includes not only the free induction decay signal derived by means of what is termed "a 90° pulse", but also the echo signal derived by means of what is called "a 90°-180° pulse".

Figure 6:
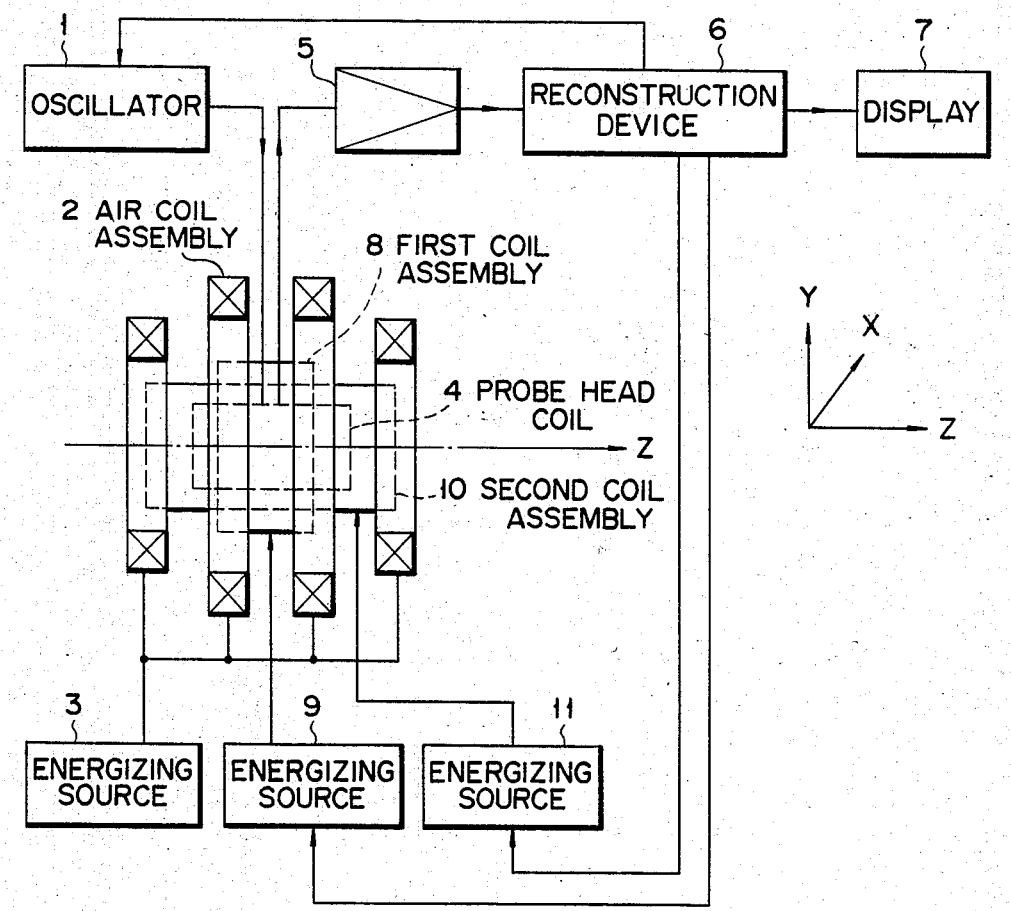
FIG. 6 shows a schematic diagram of the complete diagnostic apparatus according to the invention.

FIG. 6 is a schematic diagram of the construction of the NMR apparatus in accordance with one preferred embodiment.

Referring to FIG. 6, reference numeral 1 denotes an oscillator for generating the selective exciting pulse $H_1$; 2, an air coil assembly for generating the steady field $H_0$; 3, an energizing source or coil driver; 4, a probe head coil for applying an RF pulse to the object (not shown) and detecting a free induction decay signal FID of a nuclear magnetic resonance signal (referred to "NMR" signal); 5, an amplifier for detecting and amplifying the free induction decay signal detected by the probe head coil 4; 6, a reconstruction device for reconstructing a tomographic image from the free induction decay signals FID (referred to "FID" signals) scanned in a plurality of projection directions; 7, a display for displaying the tomographic image (of the cross-sectional slice of the object) reconstructed by the reconstruction device 6; 8, a first coil assembly comprising, e.g., a plurality of coil pairs to generate the gradient field $G_z$ having a gradient with respect to the z-axis; 9, an energizing source having a switch circuit to switch a current flowing through the first coil assembly 8; 10, a second coil assembly for generating the gradient fields $G_x$ and $G_y$ having gradients with respect to the x- and y-axes, respectively; and 11, an energizing source of the second coil assembly 10.

FIG. 7 is an illustrative representation of the first coil assembly 8 consisting of a plurality of coil pairs to generate the gradient field $G_z$. In this example, the first coil assembly 8 consists of three coil pairs 8-1, 8-2 and 8-3. The first coil pair 8-1 consists of two coil halves. FIG. 8 is a graphic representation of the gradient field strength of the coil pairs 8-1 to 8-3. Gradient fields $G_z$ generated by the coil pairs 8-1, 8-2 and 8-3 from the left to right are designated by (8-1), (8-2) and (8-3), respectively. An exciting current successively flows in the coil pairs 8-1, 8-2 and 8-3 in a given order, and the x,y plane along which the strength of the gradient field $G_z$ generated by the coil pairs becomes zero is sequentially shifted from the left to right in this drawing. The cross-sectional planes obtained by the coil pairs 8-1, 8-2 and 8-3 are designated by S1, S2 and S3, respectively, which are referred to "cross-sectional slice regions" or simply "slices".

Figure 2:
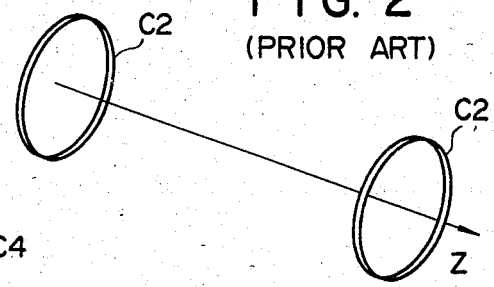
FIG. 2 shows the $G_z$ coil to be used in the NMR apparatus.
Figure 1B:
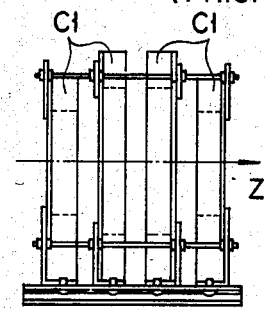
FIG. 1B shows a side view of the air coil shown in FIG. 1A.
Figure 3:
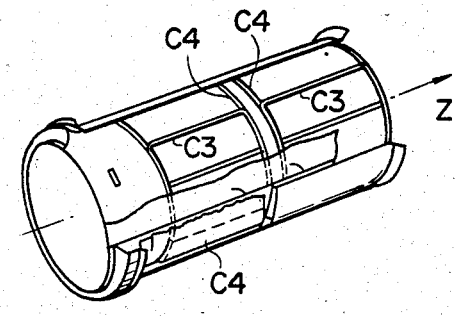
FIG. 3 shows typical $G_x$ and $G_y$ field coils in a practical NMR apparatus.
Figure 4:
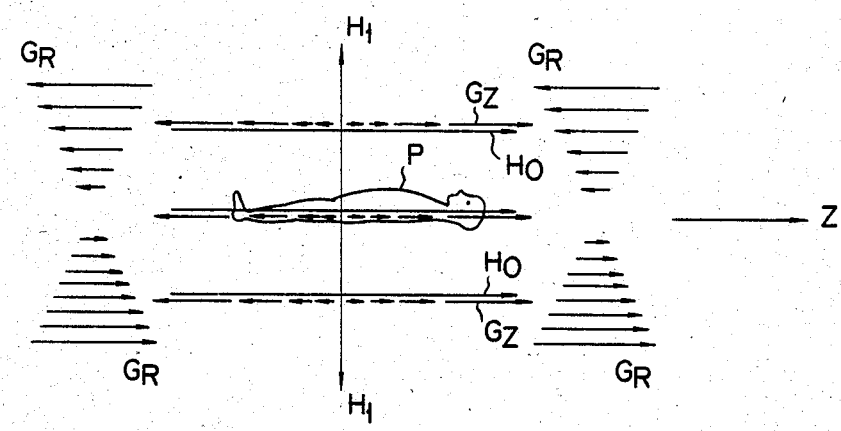
FIG. 4 shows the relationship of the $G_R$ field to other fields.
Figure 5:
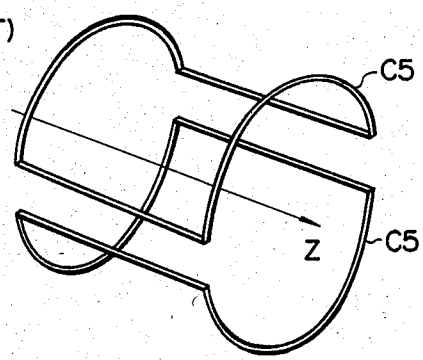
FIG. 5 shows the $H_1$ field coil in that NMR apparatus.

As is apparent from FIG. 7, reverse exciting currents need to flow in the coil halves of each of the coil pairs 8-1, 8-2 and 8-3 as in the case with reference to FIG. 2. The gradient field $G_z$ obtained in this manner has the same direction (z-axis direction) as that of the steady field $H_0$ generated by the air coil assembly 2. The field strength of the $G_z$ coil is zero at a central plane of a pair of coil halves. The directions of the field components of the $G_z$ coil oppose each other with respect to the central plane and have absolute values which linearly increase when spaced apart from the central plane (see FIG. 4).

The examination operation of the diagnostic apparatus of the first embodiment will be described with reference to the timing chart in FIG. 9.

An object (not shown) is placed in the air coil assembly 2 and the uniform steady field $H_0$ generated by the air coil assembly 2 is applied to the object. The selective exciting pulse $H_1$ is generated from the oscillator 1 in accordance with a timing signal from the reconstruction device 6 so as to apply an RF pulse field to the object through the probe head coil 4. The energizing source 9 selects one coil pair of the first coil assembly 8 in accordance with the timing signal from the reconstruction device 6 and a slice selection signal output and supplies a current through the selected coil pair. The leftmost waveforms in FIG. 9 indicate the timings when the coil pair 8-1 is selected. The gradient field $G_z$ along the z-axis and the selective exciting pulse $H_1$ are simultaneously applied to the object. When a carrier frequency $\omega_0$ of the selective exciting pulse $H_1$ is preset to be a value corresponding to the steady field $H_0$, only nuclei in the first cross-sectional slice S1 shown in FIG. 8 are excited.

When collection of free induction decay signals FID by the probe head coil 4 with respect to the first coil pair 8-1 is completed, the energizing current flows through the second coil pair 8-2 in accordance with the slice selection signal from the reconstruction device 6. In this case, the resultant gradient field $G_z$ and the selective exciting pulse $H_1$ which are the same as those described above are simultaneously applied to the object, so that free induction decay signals FID are collected by the probe head coil 4 with respect to the second slice S2 (see FIG. 8). It should be noted that the signal collection from the first and second slices S1 and S2 is performed in the same projection direction (x,y plane). This condition remains the same in signal collection from the third slice S3. Signal collection from the third slice S3 is performed using the same method and under the same conditions as described above. As a result, successive collection of FID signals for a plurality of slices (i.e., three slices S1, S2 and S3) at the first projection direction (angle) is completed during the first examination period.

The correlations of the gradient field $G_z$, the selective exciting pulse $H_1$, the resultant gradient field $G_R$, and the FID signal will be described with reference to the timing chart of FIG. 9.

Figure 9:
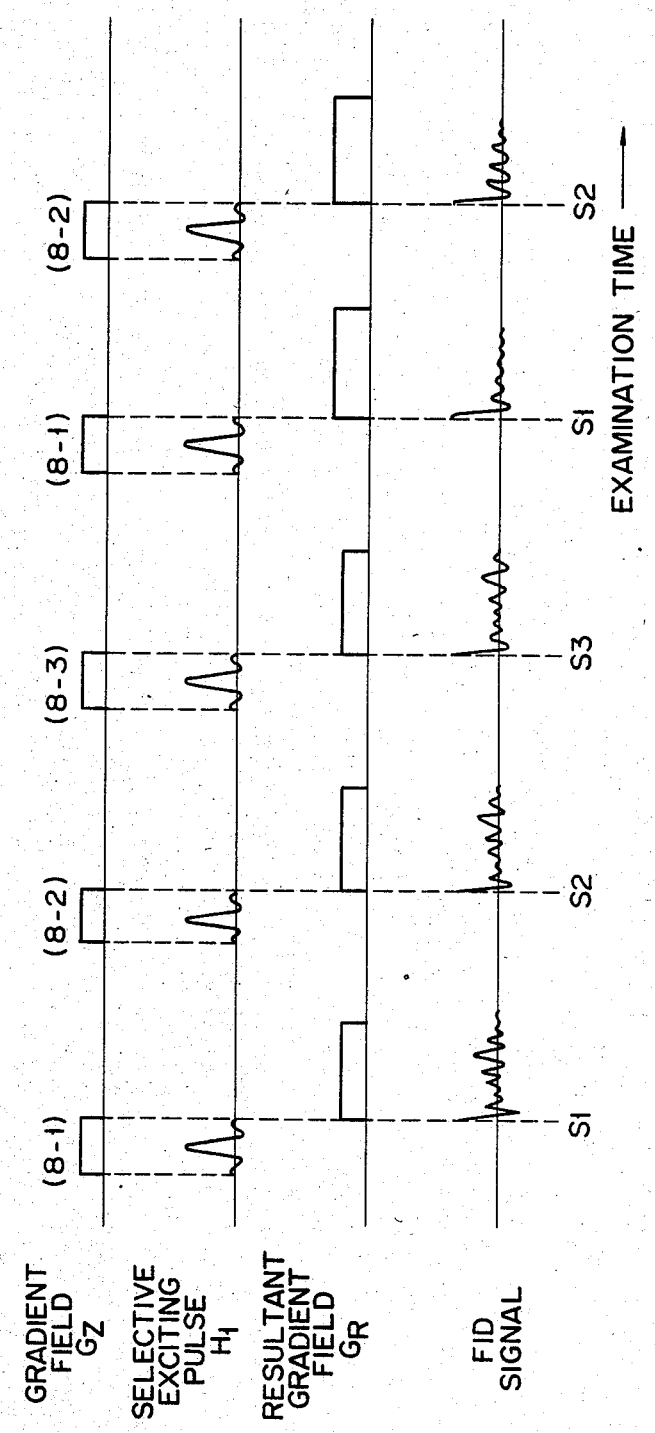
FIG. 9 is a timing chart for explaining the examination operation of a first embodiment.

As is apparent from FIG. 9, the gradient field $G_z$ generated by the coil pair 8-1 is applied together with the selective exciting pulse $H_1$ to an object (not shown). When application of the gradient field $G_z$ to the object is finished, the resultant gradient field $G_R$ generated by the second coil assembly 10 is applied to the object, thereby determining the first projection direction (angle) with respect to the x,y plane and hence obtaining the FID signals at this projection direction. While the selective exciting pulse $H_1$ and the gradient field $G_z$ are applied to the object in the same manner as in the first examination period, a timing signal and $G_x$ and $G_y$ preset signals are supplied from the reconstruction device 6 to the energizing source 11 to determine a gradient (second projection direction) with respect to the x,y plane in the second examination period. As a result, when the resultant gradient field $G_R$ (combined magnetic field of gradient components $G_x$ and $G_y$) is applied to the first slice S1 of an object (not shown), the FID signals in the second projection direction are collected. Immediately thereafter, an examination in the second projection direction is performed for the next, or second slice S2, thereby collecting the FID signals. Thereafter under the same conditions as described above, signal collection for the third slice S3 is performed. As a result, continuous signal collection during the second examination period in the second projection direction is completed.

FID signal collection is performed by a series of continuous examinations in all projection directions (360°) so as to reconstruct the tomographic images of the plurality of slices.

The projection signal indicating the density distribution of the specified nuclei in the slice is subjected to the inverse Fourier transform to obtain the FID signal. This FID signal is detected by the probe head coil 4 and is amplified by the amplifier 5. The amplified signal is then supplied to the reconstruction device 6. The reconstruction device 6 performs a predetermined operation in accordance with a time sharing system to obtain a desired tomographic image signal, thereby displaying it as a CT image on the display 7.

The above examination technique is an application of the first principle.

A second embodiment of the present invention which applies the second principle will now be described with reference to FIGS. 6 to 8 and FIG. 10.

The entire construction of the second embodiment is substantially the same as that of the first embodiment, except that a reconstruction device 6 generates a timing signal and a slice selection signal in a different manner. This difference will be described in detail later; but it can be achieved by controlling the reconstruction device 6 in accordance with a known programming method.

In order to readily understand the second embodiment, it is assumed that NMR diagnosis is performed for only three slices S1 to S3.

An object (not shown) is placed in the air coil assembly 2, and the steady field $H_0$ generated by the air coil assembly 2 is applied to the object. A timing signal is supplied from the reconstruction device 6 to the oscillator 1, so that the selective exciting pulse $H_1$ is generated by the oscillator 1. This pulse is applied as an RF field pulse to the object through the probe head coil 4. Meanwhile, the timing signal and a slice selection signal are supplied from the reconstruction device 6 to the first energizing source 9, so that an energizing current flows in the first coil pair 8-1 of the first coil assembly 8. As a result, the first slice S1 is selected as an examination object.

In the first step of the first examination period, a first resultant gradient field $G_R$, which defines a first projection angle, generated by the second coil assembly 10 driven by the second energizing source 11 (the first coil pair 8-1) is applied to the object immediately after the selective exciting pulse $H_1$ is applied thereto. When the direction of the field $G_R$ is defined as the first projection direction (angle), the FID signal from the first slice S1 in the first projection direction is obtained as a leftmost waveform shown in FIG. 10. The FID signal is received by the probe head coil 4.

In the second step of the first examination period, another gradient field $G_z$ and the same selective exciting pulse $H_1$ are applied to the object, so that the second slice S2 is selected. This second gradient field $G_z$ is generated by energizing the second coil pair 8-2. Immediately after this selection, the timing signal and $G_x$ and $G_y$ preset signals are supplied from the reconstruction device 6 to the second energizing source 11, so that the second projection direction is determined and a second resultant gradient field $G_R$ is applied to the second slice. Therefore, the FID signal from this second slice S2 in the second projection direction can be obtained by the probe head coil 4.

In the third step of the first examination period, another gradient field $G_R$ different from those in the first and second steps and the same selective exciting field $H_1$ are applied to the object to determine the third slice S3. Immediately after this application, the reconstruction device 6 causes the second energizing source 11 to generate a third resultant gradient field $G_R$ to determine the third projection direction. The resultant gradient field $G_R$ in the third projection direction is applied to the object, so that the FID signal from the third slice S3 in the third projection direction can be obtained.

Thus the first examination period is completed by the series of continuous examination steps described above. The second examination period is then started.

In the second examination period, the first slice S1 is examined in a projection direction (second projection direction) different from the above-described projection direction (first projection direction) for the slice S1 during the first examination period. More particularly, the first coil pair 8-1 is excited to generate the first gradient field $G_z$, and at the same time the selective exciting pulse $H_1$ is applied to the object. Thereafter, the second coil assembly 10 is energized to apply the second resultant gradient field $G_R$ in the second projection direction. As a result, the FID signal from the first slice S1 in the second projection direction can be obtained through the probe head coil 4.

In the same manner as described above (i.e., by collecting a series of FID signals at different projection angles (directions) of respective slices), predetermined reconstruction processing is performed, and a CT image is displayed on the display 7.

It should be noted that the waveform shape of the selective exciting pulse $H_1$ and the carrier frequency $\omega_0$ are held constant throughout the examination.

Figure 10:
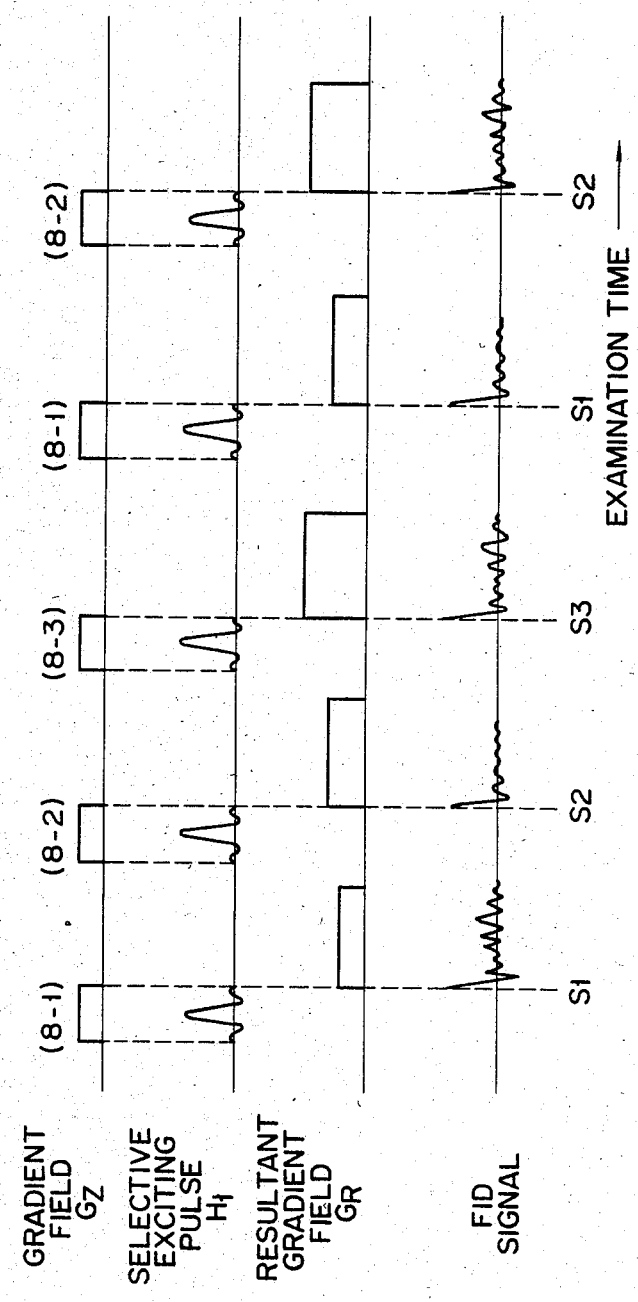
FIG. 10 is a timing chart for explaining the examination operation of a second embodiment.

It should also be noted that the resultant gradient field $G_R$ along the x,y plane is held constant during signal collection from the slices S1 to S3 in FIGS. 9 and 10.

Figure 11:
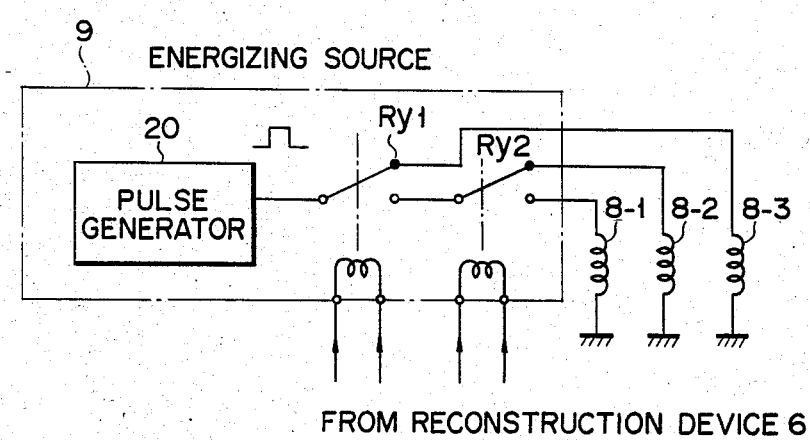
FIG. 11 is a circuit diagram of the practical energizing source.

A switching circuit for the energizing source 9 e.g., a current source is illustrated in FIG. 11. A pulse output from a pulse generator 20 is switched by relays $R_y1$ and $R_y2$ to switch the coil pairs 8-1 to 8-3 in a given order.

The NMR examination operation just described may be summarized as follows.

In order to examine one slice from different projection angles (directions) during one examination period in the conventional examination operation, a "wait time" of about 3 to 5 times T1 (where T1 is the spin-lattice relaxation time) is required to reexamine the slice at a different projection direction.

However, according to the diagnostic apparatus of the present invention, the NMR signal from the first slice S1 is collected in the first projection direction, and then the NMR signal from the second slice S2 is collected in the same or a different projection direction, and the NMR signal collection from the third slice S3 is performed within the first examination period. Thereafter, when the NMR signal collection for the first slice is performed in the second projection direction during the second examination period, a time period of at least 3 to 4 times T1 has elapsed, thereby preventing the saturation phenomenon and degradation of the S/N ratio.

During the wait time of the apparatus, signal collection of other slices can be performed, thereby substantially shortening the examination total time. At the same time, NMR signals for a plurality of slices can be obtained substantially simultaneously, resulting in convenience. If signal collection time generally falls within 50 msec to 100 msec for one slice (one projection angle), and the wait time is generally 600 msec, six to twelve slices can be substantially simultaneously scanned within this wait time. As a result, the examination total time can be shortened to 1/6 to 1/12 the conventional examination total time.

While the invention has been described in terms of certain preferred embodiments, and exemplified with respect thereto, those skilled in the art will readily appreciate that various modifications, changes, omissions and substitutions may be made without departing from the spirit of the invention.

In the above embodiments, a "90° pulse" is used as the selective exciting pulse for NMR signal collection. However, for example, an echo signal by a "90°-180° pulse" or an inverted gradient field may be used.

An air core resistive magnet or a superconducting air core magnet may be used as the air core assembly for generating the steady field.

Figure 12:
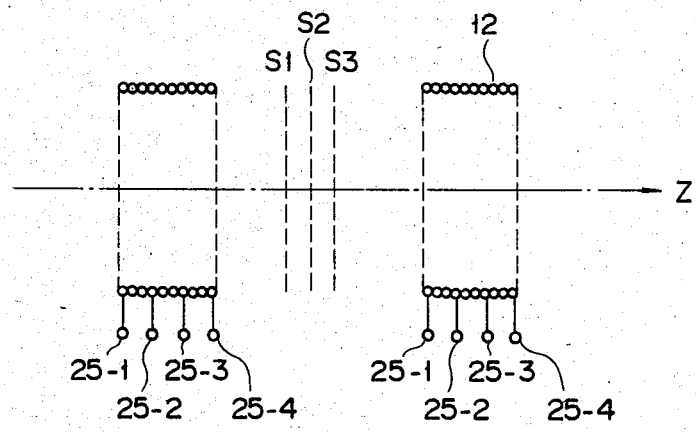
FIG. 12 shows a $G_z$ coil according to another embodiment.

Furthermore, as shown in FIG. 12, taps 25-1, 25-2 25-3 and 25-4 can be equidistantly arranged on each coil half of a pair of solenoid coils 12, thereby providing a plurality of coil pairs. In this case, the solenoid coil is easy to assemble and the slice regions are disposed adjacent to each other.

What is claimed is:

1. An apparatus for examining an object by nuclear magnetic resonance comprising:
   means for applying to the object a steady magnetic field along a longitudinal axis thereof;
   first coil means including a plurality of coil pairs, each of which is arranged along said longitudinal axis and is selectively energized so as to apply selectively to the object one of a plurality of first gradient fields, which in conjunction with said steady field gives a predetermined field in one of a plurality of slices of said object, the field direction of said first gradient field being parallel to that of said steady magnetic field and the field strength thereof changing linearly in an opposite manner along said longitudinal axis;
   means for oscillating RF pulses and applying the same through probe head means to at least one of said slices of the object in a direction perpendicular to said longitudinal axis so as to excite a nucleus in one of said slices to which is being applied said predetermined field combined between the steady magnetic field and the first gradient field, said probe head means detecting a nuclear magnetic resonance signal derived from one of said slices of the object;
   second coil means for applying selectively one of a plurality of second gradient fields to one of said slices after application to each of said first gradient field to the same is completed, the field direction of said second gradient field being parallel to said steady magnetic field and the strength of said second gradient field being gradient at a right angle with respect to that of said steady magnetic field; and
   reconstruction means which receives the nuclear magnetic resonance signals obtained from one of said slices through said probe head means with respect to a plurality of projection directions corresponding to the direction of said plurality of second gradient fields, and reconstructs a plurality of computerized tomography images for the nuclear density of said plurality of slices based upon the nuclear magnetic resonance signals.

2. An apparatus as claimed in claim 1, wherein said means for applying steady magnetic field is constructed by an air core resistive magnet.

3. An apparatus as claimed in claim 1, wherein said means for applying steady magnetic field is constructed by a superconducting air core magnet.

4. An apparatus as claimed in claim 1, wherein said plurality of coil pairs of the first coil means is constructed by a plurality of Maxwell pairs, each Maxwell pair being disposed from one another an equivalent distance apart.

5. An apparatus as claimed in claim 1, wherein said plurality of coil pairs of the first coil means is constructed by a solenoid coil sub-divided by a plurality of taps, each tap being spaced from each other at an equivalent distance.

6. An apparatus as in claim 1 further including:
   RF pulse generating means for producing RF pulses of fixed frequency; and
   switching means, coupled to said plurality of coil pairs and connected to receive said RF pulses produced by said generating means, for successively applying said RF pulses to said plurality of coil pairs in a predetermined sequence.

7. An apparatus as in claim 1 wherein:
   said plurality of coil pairs are spaced apart from one another by predetermined distances; and
   each of said coil pairs determined a different slice through said object, the distance between the slice determined by a first of said plurality of coil pairs and the slice determined by a second of said plurality of coil pairs being related to the spacing between said first and second coil pairs.

* * * * *